United States Patent [19]
Jaeger

[11] Patent Number: 6,013,485
[45] Date of Patent: Jan. 11, 2000

[54] LOW-MOLECULAR WEIGHT ACTIVE INGREDIENT EXTRACT FROM YEASTS AND METHOD FOR PRODUCING IT

[75] Inventor: Christa Jaeger, Luzern, Switzerland

[73] Assignee: Thymopharma, AG, Switzerland

[21] Appl. No.: 08/956,458

[22] Filed: Oct. 23, 1997

Related U.S. Application Data

[62] Division of application No. 08/768,622, filed as application No. PCT/EP96/01886, May 7, 1996.

[51] Int. Cl.$^7$ ..................................................... C12P 21/04
[52] U.S. Cl. ........................ 435/71.1; 435/940; 435/942
[58] Field of Search ........................ 435/41, 71.1, 255.2, 435/940, 942

[56] References Cited

U.S. PATENT DOCUMENTS

| | | | |
|---|---|---|---|
| 3,929,578 | 12/1975 | Urakami | 435/247 |
| 4,409,246 | 10/1983 | Stewart et al. | 435/255.2 |
| 4,797,359 | 1/1989 | Finkelstein | 435/68 |

FOREIGN PATENT DOCUMENTS

| | | |
|---|---|---|
| 1179957 | 5/1982 | Canada . |
| 1179957 | 12/1984 | Canada . |
| 0 065 246 | 8/1985 | European Pat. Off. . |
| 0286033 | 10/1988 | European Pat. Off. . |
| 2 175 804 | 12/1986 | United Kingdom . |
| 96/00579 | 1/1996 | WIPO . |

OTHER PUBLICATIONS

Miller et al. Proc. Natl. Acad. Sci. USA, vol. 76, No. 10, pp. 5222–5225, 1979.
Gropper et al. Exp. Myc., vol. 17, pp. 46–54, 1993.
Barnes et al. J. Bacteriol., vol. 169, No. 12, pp. 5622–5625, 1987.
Reading et al. Nature, vol. 337, pp. 655–659, 1989.
Goloubinoff, et al., GroE heat–shock proteins promote assembly of foreign prokaryotic ribulose bisphoshate carboxylase oligomers in Escherihia coli, Nature, vol. 337, Jan. 5, 1989, pp. 44–47.
Reading, et al., Characterization of the yeast HSP60 gene coding for a mitochondrial assembly factor, Nature, vol. 337, Feb. 16, 1989, pp. 655–659.
Nicolet et al., Methods in Enzymology, vol. 194, "guide to Yeast Genetics and Molecular Biology", pp. 3638, 717 (1989).
Barnes, et al., "Production of Heat Shock . . . cerevisiae", Journal of Bacteriology, Dec. 1987, p. 5622–5625.
Gropper, et al., "Inhibitors . . . Saccharomyces cerevisiae", Experimental Mycology 17, pp. 46–54 (1993).
Loppnow, et al., "IL–1 Induction–Capacity . . . Structures", The Journal of Immunology, vol. 142, pp. 3229–3238, No. 9, May 1, 1989.
Miller et al., "A response of protein . . . Saccharomyces cerevisiae", Proc. Natl. Acad. Sci, USA, vol. 76, No. 10, pp. 5222–5225, Oct. 1979.
Loppnow et al., "[1] Induction of cytokines . . . Products", Methods in Enzymology, vol. 236, pp. 3–10.
Jaffe et al., "culture of Human Endothelial Cells Derived from Umbilical Veins", The Journal of Clinical Investigation, vol. 52, Nov. 1973, pp. 2745–2756.
Ross, et al., "Morphogenesis of vascular smooth muscle in . . . culture", Ch. 3, pp. 69–91.
Loppnow, et al., "Adult Human . . . IL1", Cellular Immunology 122, pp. 493–503 (1989).
Loppnow et al., "Proliferating or Interleukin . . . Interleukin 6", J. Clin. Invest., vol. 85, Mar. 1990, pp. 731–738.
Loppnow et al., "Functional Significance . . . Pathways", Experimental Cell Research 198, pp. 283–290 (1992).
Van Snick et al., "Purification and . . . hybridomas", Proc. Natl. Acad. Sci. USA, vol. 83, pp. 9679–9683, Dec. 1986.
Gillis et al., ". . . Cell Growth Factor: Parameters . . . Activity", The Journal of Immunology, vol. 120, No. 6, pp. 2027–2032, Jun. 1978.

*Primary Examiner*—Leon B. Lankford, Jr.
*Assistant Examiner*—Christopher R. Tate
*Attorney, Agent, or Firm*—Cushman Darby & Cushman IP Group of Pillsbury Madison & Sutro LLP

[57] ABSTRACT

The invention relates to low-molecular, metabolism-activating mixtures of active ingredients from yeast fungi of the order Saccharomycetes and is characterized in that they are obtained from yeasts of the said order of Saccharomycetes, which are cultivated for some hours at temperatures starting at 37° C., are heated to a maximum of 45° C. and, following cooling, are subsequently processed in a manner known per se.

12 Claims, No Drawings

LOW-MOLECULAR WEIGHT ACTIVE INGREDIENT EXTRACT FROM YEASTS AND METHOD FOR PRODUCING IT

This is a division of application Ser. No. 08/768,622, filed Dec. 18, 1996, which is a continuation of PCT/EP96/01886 filed May 7, 1996.

The invention relates to low-molecular weight active ingredients from yeasts and to a method for producing same.

Yeast extracts from yeast fungi of the order Saccharomycetes, as well as their anabolic and respiration-stimulating and generally metabolism-activating effects, are known. Methods for obtaining such extracts have been described, for example, in EP-B 0 065 246. In this method, after a proteolytic enzyme had been added at the time of optimum fermentation, a suspension of the yeast fungus is subjected to an ultrasonic treatment until the temperature had been noticeably increased. Although the use of ultrasonics for the dialysis of yeast cells is an effective means for obtaining the extracts, it has been found that the ultrasonic treatment has quite negative side effects, since practically all compounds in an aqueous solution are subjected to a more or less pronounced oxidation. Thus, no genuine active agents are extracted from the cells in the course of the treatment with ultrasonics, instead, as a rule they are chemically altered compounds.

There is still a demand for yeast extracts and methods for producing them, which result in as genuine as possible a product and have the lowest possible content of substances altered by the production method.

To attain this object, yeast extracts in accordance with claim 1 are proposed, as well as methods for their production in accordance with claim 2.

It has been surprisingly found that it is possible to produce yeast extracts with metabolism-activating effects in a qualitatively and quantitatively improved form, if the cultures are subjected in a defined manner to a temperature change. In accordance with the invention the yeasts, which are maintained at approximately 15° C. prior to preparing the culture, are suspended in water, wherein the ratio of yeast:water is approximately 1:2. Subsequently an amount of sugar, in particular saccharose, which can be fermented with the respective yeast, is admixed in amounts of 5 weight-%. The mass is then heated to the optimum cultivation temperature of 37° to 38° C. and maintained at this temperature for at least 3 hours, and brief stirring and aerating is performed at set intervals. This generation time of the yeasts is approximately 60 minutes.

After three hours of cultivation, the mass then is heated relatively quickly to maximally 45° C. and maintained at that temperature for 60 minutes. Subsequently the suspension is allowed to slowly cool to 25° C. during a period of 60 minutes and is maintained at this temperature for approximately 60 minutes. Thus the total time of the production process lasts approximately 6 hours.

The temperature resistance of the yeasts is improved by increasing the cultivation temperature to maximally 45° C. during a generation time, and the total metabolism is clearly increased. It is assumed that the increased yield of low-molecular weight, metabolism-active ingredients is the result of the increased metabolization during the increased growth temperature. This assumption is supported in that heat shock proteins can be found in the active ingredient concentrate. Heat proteins, hsp for short, are proteins which are briefly synthesized at greatly increased rates by living cells during thermal or chemical stress. Their exact function is not yet known, but they are essential for surviving stress situations, and it is suspected that they initiate or support the ATP-dependent refolding of denatured proteins. Proteins of the hsp family 60 and 70 are contained in the yeast hydrolizates. Isolation and proof of hsp are described, for example, in Nature (London) 337, 655 to 659 and 44 to 47 (1989).

*Saccharomyces cerevisiae*, also in various pure culture forms, or *Saccharomyces uvarum* or *Saccharomyces rosei*, are preferably used as the yeasts.

Following the approximately total culture time of 6 hours, the mass is comminuted with the aid of suitable mechanical mills, such as colloid mills. If necessary, comminution can also be performed following the enzyme addition. Then the mass is reacted at approximately 37° to 38° C. with a proteolytic enzyme or a mixture of such enzymes, wherein the ratio of enzyme:biomass should be approximately 0.03:1. The reaction time is a function of the type of proteolytic enzyme used and as a rule is approximately 180 minutes. Papain, ficine or bacterial or fungal proteases are preferably employed.

Following solubilization, the entire suspension is heated inside of 30 minutes to 85° C. for activating the enzyme, and is maintained at this temperature for 30 minutes. After cooling, the mass is centrifuged, wherein the sediment can be washed one more time if required. The residue containing the active ingredients sought is filtered and concentrated at temperatures not above 40° C. in vacuo. Subsequently this solution can be subjected to usual and known spray-drying granulation.

The mixtures of active ingredients in accordance with the invention present clearly elevated metabolic activities in comparison with the mixtures of active ingredients known so far and produced in accordance with other methods, which, in the fibroblast test, as a rule are clearly higher, in part by 50 to 100%, than those of the products known up to now.

The mixtures of active ingredients in accordance with the invention can be employed in human medicine and veterinary medicine in all those cases in which an activation of the metabolism is necessary, for example for encouraging the healing of slow-healing wounds, for improved utilization of food, in particular in stock-breeding and pisciculture. A further area of use is in the field of stimulating the activities of microorganisms in enzymatic processes when treating foodstuffs.

The invention will be described in detail below by means of an example:

10 kg of *Saccharomyces cerevisiae* of the bottom yeast culture type are reacted with 20 kg of purified and filtered water of drinking water quality in a reactor. This suspension is provided with 5 weight-% of saccharose and well mixed by stirring. Then the suspension is heated to 37° to 38° C. and maintained at this temperature for at least 3 hours, wherein brief stirring and aeration is performed at intervals of approximately half an hour. Following this the mass is heated to 45° C. and maintained for sixty minutes at this temperature, and afterwards again cooled to 25° C. over a period of time of 60 minutes and maintained there for 60 minutes.

Subsequently the balanced suspension is reacted with an appropriate amount of papain, wherein the ratio of enzyme:biomass should be 0.003:1. Following the enzyme addition with simultaneous comminution of the yeasts, the mixture is stirred for 180 minutes at 37° to 38° C. Then the mixture is heated to 85° C. within 30 minutes and maintained at this temperature for 30 minutes, and then cooled and centrifuged. The centrifuged material is drawn off and the sediment is washed again, and again centrifuged. The centrifuged materials are combined and then, following filtration, concentrated at temperatures below 40° C., preferably with the aid of a vacuum evaporator. The concentrated solution which is free of cells is then subjected in a manner known per se to spray-drying granulation.

I claim:

1. A method for producing a mixture of low-molecular weight, metabolically active ingredients comprising heat shock proteins of one or both of the families hsp 60 and 70, by:

(a) cultivating live Saccharomycetes yeast which contain heat shock proteins of one or both of the families hsp 60 and 70, in a solution at a temperature between 37–38° C., (b) subsequently heating the yeast solution to about 45° C., (c) slowly cooling the yeast solution to 25° C., and (d) isolating from the yeast solution a mixture of low-molecular weight, metabolically active ingredients comprising heat shock proteins of one or both of the families hsp 60 and 70, wherein the yeast remains viable and intact throughout steps (a), (b) and (c).

2. The method according to claim 1, wherein in step (a) the yeast solution is cultivated at a temperature between 37–38° C. for 2–6 hours, in step (b) the yeast solution is heated to 45° C. for 40–80 minutes, and in step (c) the yeast solution is cooled to 25° C. within 40–80 minutes, and is maintained at 25° C. for about 40–80 minutes.

3. The method according to claim 1 or 2, wherein step (a) further includes adding a fermentable sugar to the yeast solution in an amount of 5%.

4. The method according to claim 1, wherein in step (a) the yeast is cultivated at a temperature between 37–38° C. for 2–6 hours.

5. The method according to claim 1, wherein the Saccharomycetes yeast is selected from the group consisting of *Saccharomyces cerevisiae, Saccharomyces uvarum* and *Saccharomyces rosei.*

6. The method according to claim 2, wherein in step (b) the yeast solution is heated to 45° C. for 40–80 minutes.

7. The method according to claim 2, wherein in step (c) the yeast solution is cooled to 25° C. for 40–80 minutes.

8. The method according to claim 1 or 2, wherein step (d) includes comminuting and enzymatically solubilizing the yeast in the presence of proteolytic enzymes at a temperature of 37°–38° C., heating the yeast solution above 80° C. to effect activation of the proteolytic enzymes, centrifuging the yeast solution, and isolating a mixture of low-molecular weight, metabolically active ingredients and heat shock proteins of one or both of the families hsp 60 and 70 is isolated therefrom.

9. The method according to claim 8, wherein the proteolytic enzyme is papain.

10. The method according to claim 9, wherein the proteolytic enzyme is papain, ficine, bacterial protease or fungal protease.

11. The method according to claim 8, wherein the ratio of proteolytic enzymes to yeast in step (d) is approximately 0.003:1, by weight.

12. The method according to claim 8, wherein *Saccharomyces cerevisiae* is the yeast.

* * * * *